United States Patent [19]

Bro

[11] Patent Number: 4,688,577

[45] Date of Patent: Aug. 25, 1987

[54] APPARATUS FOR AND METHOD OF MONITORING AND CONTROLLING BODY-FUNCTION PARAMETERS DURING INTRACRANIAL OBSERVATION

[76] Inventor: William J. Bro, 3735 W. Cavalier Dr., Phoenix, Ariz. 85019

[21] Appl. No.: 827,866

[22] Filed: Feb. 10, 1986

[51] Int. Cl.⁴ .............................................. A61B 5/02
[52] U.S. Cl. .................................. 128/670; 128/691; 128/748; 604/49; 604/50; 604/66
[58] Field of Search ..................... 128/670, 691–692, 128/748; 604/50, 65, 66

[56] References Cited

U.S. PATENT DOCUMENTS

| | | | |
|---|---|---|---|
| 4,080,966 | 3/1978 | McNally et al. | 604/66 |
| 4,204,547 | 5/1980 | Allocca | 128/748 |
| 4,392,849 | 7/1983 | Petre et al. | 604/50 |
| 4,621,647 | 11/1986 | Loveland | 128/748 |

Primary Examiner—Lee S. Cohen
Assistant Examiner—David Shay
Attorney, Agent, or Firm—Joseph H. Roediger; Gregory J. Nelson

[57] ABSTRACT

A system and method for monitoring body-function parameters including bloodflow, intracranial pressure and blood pressure during cranial observation of an individual wherein different pharmacological agents are added to an intravenous fluid to compensate for changes in the parameters.

10 Claims, 2 Drawing Figures

APPARATUS FOR AND METHOD OF MONITORING AND CONTROLLING BODY-FUNCTION PARAMETERS DURING INTRACRANIAL OBSERVATION

BACKGROUND OF THE INVENTION

This invention relates to a system for monitoring intracranial pressure and intracranial bloodflow during medical observation or surgical activity taking place within the cranium.

The increasing recognition of the need for immediate attention to be given injured patients by specialists in traumatic medicine has generated a concomitant need for apparatus and procedures which provide the medical personnel with reliable information concerning the body-function parameters of the injured patient. In particular, an injury occurring on or within the cranium of an individual requires information-gathering techniques to be immediately utilized. At present, the use of intracranial pressure monitoring apparatus is recognized as necessary to provide the medical personnel information concerning increases or drops in pressure within the confines of the cranium. This measurement is found to be important since an increase in fluid pressure within the skull manifests itself as a reduction in bloodflow to the brain of the injured patient. In practice, it is customary to use a transducer which is inserted through a hole intentionally formed in the cranium. The transducer pressure serves as a sensor and is electricially similar to the well-known strain gauge bridge configuration and generates an electrical signal in response to fluid pressure changes. The output of the transducer is supplied to a monitoring device which gives a visual display of pressure variations in the cranium.

An additional monitoring device has been provided to the medical team administering to trauma patients which utilizes thermal diffusion techniques to aid in the determination of bloodflow in body tissue and is particularly well-suited for intracranial measurements. One such device suitable for use in determining cortical bloodflow is the thermal diffusion bloodflow probe set forth in my U.S. Pat. No. 4,354,504. This probe is intended to be utilized during surgery when the cranium is opened and the dura is held in place with retractors so as to enable the probe to be placed in contact with brain tissue. The probe then generates an electrical signal indicative of the bloodflow in that region of the brain.

Recently, the interaction of intracranial pressure and intracranial bloodflow has received increasing attention from medical personnel operating in this field. There is an inverse relationship between intracranial pressure and the bloodflow therein since the cranium or skull has a finite volume. The increase in pressure of fluid surrounding the brain coupled with the swelling of the brain itself has been found to result in reduced bloodflow through the network of blood vessels in the brain. Historical data indicates that as the intracranial pressure of an individual increases significantly, the patient is not likely to do well. Consequently, increasing attention is directed to the interaction between blood pressure, bloodflow and intracranial pressure.

An autoregulation system exists within the human body to cause blood vessels to dilate and thereby increase capacity to carry blood. However, it is believed that as intracranial pressure increases to a high level or increases at a very rapid rate, then the vessels are unable to either dilate further or rapidly enough. Consequently, the bloodflow in the brain is diminished as pressure increases. It is believed that the autoregulation system works for a while during initial pressure increases, thus lulling the medical observer into the situation where they believe the conditions to be following the predicted pattern. When the point is reached that the autoregulation system cannot handle the results of increasing intracranial pressure, external pharmacological agents must be introduced into the body in an attempt to stimulate bloodflow by the intentional increasing of blood pressure in the body.

Accordingly, the present invention has as a primary object the provision of a system for sensing intracranial bloodflow and pressures, monitoring these quantities for irregularities or dangerous conditions and providing an external display of information promptly to enable the medical personnel to react accordingly. A further object is the provision of a system in which a controlling function directed to the modification of fluids being introduced into the vascular system of the patient takes place without the need for independent action by the attendant personnel. Also, the system provides for interaction between the intracranial pressure monitor and the cranial bloodflow monitor so as to automatically adjust the predetermined lower limit for bloodflow in response to a high rate of increase as well as a high level of intracranial pressure.

SUMMARY OF THE INVENTION

The system, which is the subject of the present invention, is concerned with monitoring and controlling selected body function parameters during intracranial observations and surgical routines in order to enable the introduction of pharmacological agents to be timely made in order to reduce the opportunity for harm to the patient. The system includes an intracranial pressure monitor means which is disposed in part in the cranium for sensing the fluid pressure therein and generating an electrical pressure output signal indicative thereof. This pressure output signal is supplied to a first comparator which generates a first signal when the pressure output signal exceeds a predetermined limit. Thus, the first signal occurs when intracranial pressure rises above what is believed to be a danger level for this patient.

A rate detector is provided to receive the pressure output signal from the monitor and generates a rate signal when the rate of change of intracranial pressure exceeds a predetermined limit. The rate signal is indicative of rapid changes in intracranial pressure which are likely to defeat the autoregulation system of the patient in attempting to maintain adequate bloodflow to the brain.

The bloodflow in the cranium is sensed by intracranial bloodflow monitoring means which provide a bloodflow output signal, typically derived from thermal measurements taking place at the location of a heat sensing probe placed adjacent to brain tissue. A second comparator is provided for receiving this bloodflow output signal and generates a second signal when the bloodflow is less than a predetermined limit. Thus, the second signal indicates that a danger zone is about to be entered when the bloodflow is reduced below a desired minimum level.

During these medical observations which may or may not accompany the performance of a surgical technique, fluid is customarily being introduced into the vascular system of the body, typically through a conventional intravenous system. The present invention utilizes means for controlling the introduction of fluid into the vascular system of the body along with means responsive to the second output signal from the second comparator which alters the composition of the fluid in a manner which varies cranial bloodflow. Typically, this is caused by increasing or decreasing the amount of selected pharmacological agents in the fluid being introduced into the body. Further, setpoint control means is included in this system for receiving the first output signal and the pressure rate signal. This control means varies the limit which causes the second comparator to provide an output signal and thus alters the composition of the fluid being introduced into the patient at a lesser or lower observed cranial bloodflow. This control means thus operates to change the base line or danger zone bloodflow limit inversely in response to increasing intracranial pressure.

Further features and advantages of the invention will become more readily apparent from the following detailed description of a specific embodiment thereof when taken in conjunction with the accompanying drawings.

DESCRIPTION OF THE PREFERRED EMBODIMENT

Figure 1:
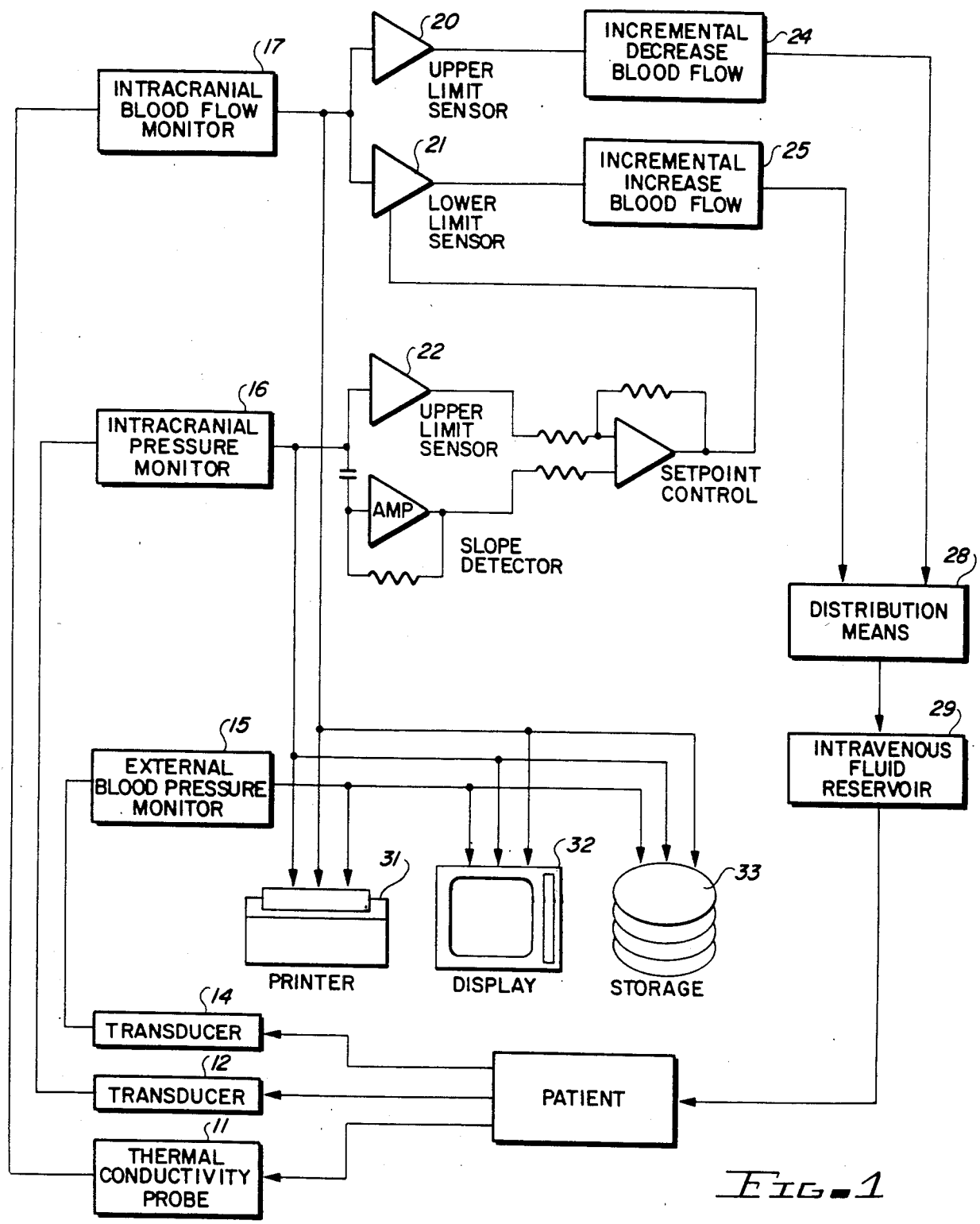
FIG. 1 is a block schematic diagram of one embodiment of the invention.

Referring now to FIG. 1, the system for monitoring and controlling selected body function parameters during observation of or the performance of operations within the cranium is shown comprising three sensing elements 11, 12 and 14 which are positioned on the body of the patient. These transducers are located to sense a particular parameter of body function and each generates a signal which is indicative thereof. Each of these transducers has its output signal coupled to a monitor which converts the input into an analog electrical signal for further processing.

During observation of patients having head injuries, the importance of monitoring to insure a sufficient minimum supply of bloodflow to the brain is recognized. In situations where injury has occurred to the cranium and perhaps to the contents thereof, the brain itself is likely to swell within the confines of the cranium thereby increasing the fluid pressure within the skull. Since the skull is inflexible and defines a finite volume, the swelling of the brain not only increases the external pressure on the brain but also results in this pressure being transmitted through the brain to decrease the vascular capacity of the brain tissue itself. The body has an autoregulation system which, up to a point, is able to compensate for reduced bloodflow by automatically dilating blood vessels within the affected area of the brain. However, this autoregulation system is found to cease functioning when the absolute blood pressure of the patient drops to a level, which level is an individual one for each patient.

Historically, the rapid rise of cranial pressure has indicated that the patient's chances of normal recovery have diminished. This is frequently due to the fact that the autoregulation system has ceased to function. In a situation where the dilation mechanism is no longer effective, pharmacological agents can be introduced into the body to raise the blood pressure and enhance the bloodflow through the brain. At the same time, observations must be made to insure that an aneurysm has not occurred since the indicators would show a high bloodflow in the brain especially in the region being monitored and a high intracranial pressure. At the same time, the external blood pressure readings might not show a low level. In such a circumstance, the agents added to the fluid being supplied to the patient must be altered so that the blood pressure is reduced preparatory to the performance of a surgical technique.

When a patient has suffered a traumatic injury to the brain, conventional medical techniques call for the immediate placement of a pressure transducer in the cranium to sense fluid pressure. Intravenous connection for the introduction of fluid into the patient is made at the same time. The personnel monitoring the patient's condition add pharmacological agents to the fluid reservoir so that the fluid introduced promotes the desired compensating reaction to the intracranial pressure. In other words, as the brain swells because of injury, the intracranial pressure increases and the medical personnel typically add measured quantities of agents to increase bloodflow in the brain. These procedures are also practiced during surgery and in the intensive care facilities utilized for post recovery observation.

The present invention includes a pressure transducer 12 inserted into the cranium so as to contact the fluid thereon. One type of transducer successfully utilized is the model 15PC made by Micro Switch. The transducer provides an output signal which is fed to an intracranial pressure monitor 16 which converts and scales the signal into an electrical signal indicative of the pressure therein and may include a readout display. This monitor, as well as monitors 15 and 17, was a Saber CBF monitor made by Flowtronics, Inc. of Phoenix, Arizona, although other monitoring components may be utilized if desired. The output of monitor 16 is fed to an upper limit sensor 22 which provides an output signal when the pressure is above a predetermined level. The sensor is a comparator circuit, for example a National Semiconductor LM-106 Comparator, with external adjustment of the comparison level provided. Also, the output signal from the pressure monitor 16 is fed to slope detector 23 which may comprise an amplifier in combination with a capacitor and resistor as shown. The slope detector provides an output signal when the rate of change of intracranial pressure exceeds a certain predetermined rate. This rate can be externally varied to conform to the patient. The output terminals of sensor 22 and slope detector 23 are coupled to set-point control 26.

A transducer 11 for sensing intracranial bloodflow in the region adjacent to an opening in the skull through which it is inserted, is coupled to monitor 17. One such thermal conductivity probe found especially well-suited for practice in the present invention is manufactured by Flowtronics, Inc. of Phoenix, Arizona and is the subject of U.S. Pat. No. 4,354,504, issued Oct. 19, 1982 to William J. Bro. The thermal conductivity probe described therein measures bloodflow by thermal diffusion techniques. The output signal from this probe is supplied to the monitor which generates an electrical signal that is indicative of the intracranial bloodflow in the particular region of the brain being sensed. The output of monitor 17 is supplied to upper limit sensor 20 and lower limit sensor 21, each of which provide an output signal if the information signal received thereby either exceeds or is less than their corresponding limits. These sensors are, in effect, comparators which provide an output signal only in the case that the input thereto reaches a predetermined level. The upper limit sensor 20 generates an output signal when bloodflow exceeds a certain level and is supplied to an incremental decreasing control device 24 which is coupled to distribution means 28. Similarly, the lower limit sensor 21 has its output coupled to an incremental increasing control circuit 25 also coupled to means 28. The control devices 24 and 25 in the embodiments tested were manufactured by Sage Instrument - Model 355.

In operation, when the bloodflow is found to be without the given range, either the decreasing control circuit 24 or the increasing control circuit 25 cause the distribution means 28 to dispense measured quantities of pharmacological agents into the intravenous fluid reservoir 27 for introduction into the patient. The agents dispensed into the reservoir act to increase or decrease the cranial bloodflow accordingly. Since the data is continually fed into the monitors and compared at the sensors, incremental changes in fluid composition continue until the desired correction has been effected.

The set-point control 26 has its output signal fed to the comparator of lower limit sensor 21 and operates to reduce the lower limit at which the incremental increasing of bloodflow is called for by control circuit 25. When the intracranial pressure exceeds a certain limit or its rate of increase is beyond the limit of the slope detector 23, set-point control 26 is responsive to one or both of these conditions to automatically lower the limit of sensor 21 so that intracranial bloodflow is enhanced at a lower level.

Also, an external blood pressure monitor 15 is coupled to the patient by transducer 14, which in the embodiment tested and operated, successfully utilizes a Micro Switch 156PC transducer. The monitor provides a visual display of the overall body blood pressure at this time. As shown, the output of monitors 15, 16 and 17 are connected directly to a printer 31 for immediate readout and visual storage, a CRT display 32 for visual display of instantaneous data as well as being coupled to a storage device shown as a collection of discs 33. In one embodiment of the invention, the printer, display and storage devices used were contained in a Hewlett-Packard IPC Computer.

Figure 2:
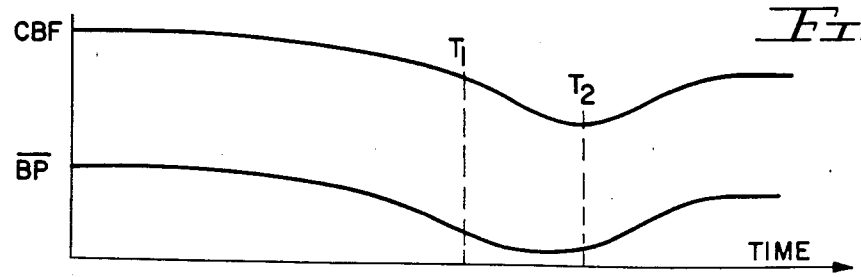
FIG. 2 shows curves illustrating the autoregulation system of the body.

Referring now to FIG. 2, the curves showing cranial bloodflow (CBF) and absolute blood pressure (BP) are shown slightly exaggerated to illustrate the breakdown of the autoregulation function of the body occurring at time $T_1$. This occurrence takes place when the dilation of the blood vessels is not sufficient to increase bloodflow and both blood pressure and bloodflow begin to rapidly decrease to a dangerously low point. The introduction of a suitable pharmacological agent to stimulate blood pressure overcomes the inability of the blood vessels to further dilate and at $T_2$ is shown causing the bloodflow and blood pressure to once again attain a safe level. The effects of the autoregulation system can be seen by the portion of the curves prior to the time $T_1$, wherein the bloodflow tends to remain relatively flat while the blood pressure begins to noticeably drop. The inability of the autoregulation system to maintain sufficient bloodflow is believed to be due to the intracranial pressure either exceeding a certain limit or rapidly increasing at a rate which the autoregulation system cannot compensate for.

In the performance of diagnostic tests to determine the injuries suffered in an injured patient, the probe 11, and transducers 12 and 14 are immediately placed upon the patient and the signals monitored. The upper limits of sensors 20 and 22 are adjusted as well as the lower limit of sensor 21 and the rate of change for slope detector 23 based on age, sex, weight and other guidelines used by the observation team. The pressure monitoring is supplementary to the bloodflow monitoring since the thrust of the process is to provide adequate bloodflow in the brain so that permanent or serious injury does not take place. The use of thermal conductivity probe, or any site specific equivalent thermal diffusion device provides an indicator of bloodflow in a localized region. This is normally adequate to predict bloodflow throughout the brain, however, additional probes can be utilized if necessary. The pressure monitoring information is required to anticipate the need to increase bloodflow rapidly in the case of a rapid rate of swelling since only a finite amount of fluid can be introduced into the cranium.

While the foregoing has referred to a particular embodiment of the invention, it is recognized that many modifications and variations may be made therein without departing from the scope of the invention as set forth in the claims.

What I claim is:

1. A system for monitoring and controlling selected body function parameters during intracranial observations, said system comprising:
   (a) intracranial pressure monitor means for sensing fluid pressure in the cranium and providing a pressure output signal;
   (b) a first comparator means for receiving the pressure output signal and generating a first output signal when the pressure output signal exceeds a predetermined limit;
   (c) rate detector means for receiving the pressure output signal from said monitor means and generating a rate signal when the rate of change of said pressure exceeds a predetermined limit;
   (d) intracranial bloodflow monitor means for sensing and providing a bloodflow output signal
   (e) a second comparator means for receiving the bloodflow output signal and generating a second output signal when said bloodflow is less than a predetermined limit,
   (f) means for controlling the rate of introduction of fluid into the vascular system of the body;
   (g) means responsive to the second output signal from said comparator means for altering the composition of said fluid to thereby vary cranial bloodflow; and
   (h) set-point control means for receiving the first output signal and the rate signal, said control means varying the predetermined limit of said second comparator means to permit the alteration of the composition of said fluid at a lesser cranial bloodflow.

2. The system of claim 1 further comprising a third comparator means for receiving the bloodflow signal and generating a third output signal when said bloodflow exceeds a predetermined limit, said means for altering the composition of said fluid being responsive to the second and third output signals from said comparator means to vary the cranial bloodflow accordingly.

3. The system of claim 2 wherein said intracranial bloodflow monitor means comprises thermal diffusion sensing means for placement within said cranium to determine bloodflow therein.

4. The system of claim 3 wherein said intracranial pressure monitor means comprises a transduce means for insertion into the cranium to determine fluid pressure therein.

5. The system of claim 4 further comprising means for monitoring the blood pressure of the body and providing a blood pressure output signal, said means being located remote from the cranium.

6. The system of claim 5 further comprising means for receiving the pressure, bloodflow and blood pressure output signals and visually displaying same.

7. A method for use in monitoring and controlling selected body function parameters during intracranial observations, said method comprising the steps:

(a) sensing intracranial fluid pressure and generating a first electrical signal representative of said pressure;

(b) setting an upper limit for said pressure and generating a limit pressure signal if said first signal exceeds said limit;

(c) setting a rate of increase limit for said pressure and generating a rate pressure signal if said first signal exceeds said rate;

(d) sensing intracranial bloodflow and generating a second electrical signal representative of said bloodflow;

(e) setting a lower limit for bloodflow and generating a lower limit signal if said second signal is less than said limit;

(f) regulating said lower limit for bloodflow in response to at least one of said limit pressure and rate pressure signals; and (g) controlling the composition of fluid introduced into the vascular system of the observed body subject in response to the lower limit signal, whereby selected body function parameters of said subject are controlled during intracranial observation.

8. The method of claim 7 further comprising the step of setting an upper limit for bloodflow and generating an upper limit signal if said second signal is greater than said limit; and controlling the composition of fluid in response to the upper limit signal.

9. The method of claim 8 further comprising the step of simultaneously displaying said first and second electrical signals.

10. The method of claim 9 further comprising the steps of sensing the blood pressure of said subject and generating a third electrical signal representative of said pressure; and simultaneously displaying said first, second and third electrical signals.

* * * * *